United States Patent [19]
May et al.

[11] Patent Number: 5,275,785
[45] Date of Patent: Jan. 4, 1994

[54] TEST DEVICE FOR DETECTING AN ANALYTE IN A LIQUID SAMPLE

[75] Inventors: Keith May, Bedfordshire; Michael E. Prior, Northamptonshire, both of England

[73] Assignee: Unilever Patent Holdings B.V., Netherlands

[21] Appl. No.: 904,888

[22] Filed: Jun. 25, 1992

Related U.S. Application Data

[63] Continuation of Ser. No. 377,849, Aug. 18, 1989, abandoned.

[30] Foreign Application Priority Data

Oct. 30, 1987 [GB] United Kingdom ............... 8725458

[51] Int. Cl.⁵ ................ G01N 33/543; G01N 33/558
[52] U.S. Cl. ...................................... 422/56; 422/57; 422/58; 435/7.9; 435/810; 435/970; 436/164; 436/169; 436/514; 436/518; 436/530; 436/805; 436/807; 436/810
[58] Field of Search ...................................... 422/55–; 436/518, 530, 164, 169, 805, 810, 807, 824, 514; 435/7.9, 810, 970

[56] References Cited

U.S. PATENT DOCUMENTS

| | | | |
|---|---|---|---|
| 4,960,691 | 2/1990 | Gordon et al. | 422/58 |
| 5,135,873 | 8/1992 | Patel et al. | 422/58 |

FOREIGN PATENT DOCUMENTS

| | | |
|---|---|---|
| 186799 | 7/1986 | European Pat. Off. |
| 239174 | 9/1987 | European Pat. Off. |
| 262328 | 4/1988 | European Pat. Off. |

*Primary Examiner*—David Saunders
*Assistant Examiner*—Christopher L. Chin
*Attorney, Agent, or Firm*—Cushman, Darby & Cushman

[57] ABSTRACT

A chromatographic test device for detecting the presence of an analyte in a liquid sample and incorporating at least two liquid-conductive zones (3, 4) which form separate liquid flow paths which deliver separate liquid streams to a region (8) in the test device during the test procedure, wherein control of the relative liquid flows in the separate flow paths is achieved, at least in part, by ensuring that at least one of the liquid flow paths is enhanced or made and/or broken or restricted during the course of the test procedure. Preferably such control is achieved by incorporating a liquid-swellable material (11) which is arranged to swell by contact with liquid sample and/or reagent and thereby to make or break contact between two liquid-conductive zones.

5 Claims, 2 Drawing Sheets

TEST DEVICE FOR DETECTING AN ANALYTE IN A LIQUID SAMPLE

This is a continuation of application No. 07/377,849, filed on Aug. 18, 1989, which is now abandoned.

This invention relates to devices and methods for chemical testing, and especially devices and methods for microchemical testing of clinical sample materials, e.g. urine, blood, serum, etc.

Some recent examples of prior art devices and methods are shown by EP 0 100 619 and U.S. Pat. No. 4,435,504 (Syva) which concern immunochromatographic assays, which exploit the specific binding of a material relevant to the assay with a binding partner carried on a filter-paper support. Similarly, combinations of bibulous support materials with immunoassay methods are the subjects of U.S. Pat. No. 4,168,146 (Kabi), U.S. Pat. No. 4,461,829 (Miles), U.S. Pat. No. 4,517,288 (American Hospital Supply), and EP 186,799 (Behringwerke).

In particular, EP 186799 (Behringwerke) describes chromatographic test devices wherein a liquid stream containing a test sample and/or other reagents flows along a porous carrier material, and the test result is developed in a detection zone in which a specific binding reagent is immobilized. In one embodiment, EP 186799 suggests that more than one body of porous carrier material can be provided in the test device, and that delayed delivery of reagents associated with a signal-developing system can thereby be delivered to the detection zone via a liquid stream that flows parallel to the main liquid stream, but more slowly. In EP 186799 it is suggested that such a parallel liquid stream can be controlled by using a more slowly chromatographing absorbent medium such as a selected chromatographic paper, or a paper that has been impregnated at places with components that temporarily block the mobile phase, such as polymers that confer a high viscosity when dissolved.

The present invention is also concerned with test devices which incorporate a plurality of liquid-conductive zones which deliver separate liquid streams to a region in the test device during the assay procedure. Although it is possible to provide such a test device in which the separate liquid-conductive zones are in permanent contact at the point at which the separate liquid streams need to come into contact with one another, and hence control of the relative liquid flows is achieved for example by the use of conductive materials having different properties as suggested in EP 186799, we believe that much greater control can be achieved if at least one of the liquid flow paths within the device is enhanced or made and/or broken or restricted during the course of the test. The present invention provides test devices having at least two liquid flow paths and wherein at least one of the flow paths incorporates a "switch" which influences the delivery of material in that flow path to another flow path within the device.

The present invention provides a test device for detecting the presence of an analyte in a liquid sample and incorporating a plurality of liquid-conductive zones which form separate liquid flow paths which deliver separate liquid streams to a region in the test device during the test procedure, wherein control of the relative liquid flows in the separate flow paths is achieved, at least in part, by ensuring that at least one of the liquid flow paths is enhanced or made and/or broken or restricted during the course of the test procedure. Preferably, the device incorporates a liquid-swellable material which is arranged to swell by contact with liquid sample and/or reagent and thereby make or break contact between two liquid-conductive zones, thereby to promote or hinder liquid flow and produce a change in reaction conditions relevant to the test.

For example, a water-swellable or aqueous liquid-swellable material can be used to make or enhance contact between a first and second conductive zone and thereby initiate or promote transfer of a washing and/or reagent liquid between the zones. Such transfer can occur for example by conduction through the conductive zones, e.g. assisted by capillarity due to the material of the zones. The material of the conductive zones can be fibrous or granular or porous solid, e.g. as glass or filter paper material, or gel granules, or a porous membrane possessing pores that communicate in the direction desired for liquid flow. If desired, the swellable material can constitute or be a part of one or both of the conductive zones between which contact is to be made by the swelling effect.

Alternatively contact between two liquid-conductive materials can be broken by the swelling effect. For example, two liquid-conductive materials can be disposed in contact with separating means for forcing them apart by the swelling of the liquid-swellable material.

'Contact' in this context related to two liquid-conductive zones means such contact as will enable liquid to flow or seep or diffuse from one to the other, whether under applied pressure or not: in any case any applied pressure (if present) is to be insufficient to drive liquid flow between the zones when a gap—most often an air gap—is present between them.

In one important embodiment of the invention, contact between liquid-conductive zones is made or formed or enhanced by swelling of a liquid-swellable material and thereby initiates or promotes flow of a washing or reagent liquid which acts to start or stop or modulate a reaction relevant to the test in one of the conductive zones.

For example, the washing/reagent liquid flow can be arranged to stop a chromogenic enzyme reaction occurring in one of the zones, e.g. by altering the aqueous-liquid pH to stop or slow the reaction down to an adequately low rate to allow reasonable time for a user to measure, inspect and/or record the chromogenic result. Alternatively, an auxiliary reagent can be introduced in the liquid flow that results from the making or promoting of contact, to start a detectable reaction or alter its course by effectively substituting one reagent and reaction for another.

The liquid-swellable material can be any solid or gel-form material that is capable of conducting the liquid (usually water or an aqueous medium), which increases substantially in volume when wetted with the liquid, and which does not have any properties which might interfere with the performance of the test or which cannot be removed or neutralized to prevent such interference. An example of a potentially interfering property would be non-specific protein binding, but this can usually be blocked by prior treatment with bovine serum albumen or polyvinylalcohol, for example. Highly-absorbant papers are available commercially and which act as "blotting paper", taking up liquid and expanding in volume to, for example, double their thickness. Other suitable liquid-swellable materials include lyogels. If the gel is granular in form, it can if desired be enclosed within an envelope of liquid-conductive material such as paper, to retain the granular material in situ during manufacture of the test device and storage of the device in the dry state before use.

The invention therefore provides superior test devices and methods for carrying out microchemical tests using liquid samples, wherein a reaction zone in a liquid-conductive zone is exposed to material inflow, e.g. liquid inflow, from at least two different routes and/or at least two different sources, especially for example applied at the same time to the device, arranged so that the reaction zone experiences inflow of liquid from the sources or routes in different proportions and/or at different times during the course of performance of the test.

The composition of the liquid arriving by each of two or more flow paths to the reaction zone can be arranged to be different, either by use of a different liquid source in each case, and/or by use of flow paths which carry or are in contact with or impregnated with a soluble or dispersible material relevant to the test, such as a reagent or diluent or washing material.

The difference in arrival time of two different liquids at the test or reaction zone, and the compositional differences of the liquid as they arrive at the zone, can be selected and adjusted at will from within a wide range to suit the particular requirements of the test or reaction in view.

For example, a competitive binding assay can be carried out by arranging one flow path to bring a sample material and labelled competitor material into contact with a specific binding agent for them both, and for another flow path later to bring in a reagent material to visualized the bound label, after the sample and competitor (in so far as they remain unbound) have been washed out of the reaction zone into an absorbent sink or reservoir by liquid from either flow path or both.

Suitable liquid-conductive materials to compose the flow paths and reaction zone are for example porous, granular and fibrous materials. To supplement the "switching" feature of the invention, a useful method of assuring inflow of liquid from two different routes or sources at two different times into the reaction zone although they may be applied to the test device at the same time, is to use liquid-conductive connecting zones, lines or tracks of different liquid-conductive rate, e.g. achieved by selection of different porosity, fibrous fineness, or other feature affecting liquid conduction.

In general, a test device of the invention incorporates a liquid-conductive region which carries a reagent specific for the test to be carried out, e.g. in immobilized form. Such a reagent can for example be a specific binding reagent such as an antigen or antibody, and can if desired be immobilized on the liquid-conductive carrier by methods well-known per se for adsorbing or coupling such materials to solid carriers, e.g. by physical adsorption to plastics or cellulose-based material or by covalent coupling using per se well-known coupling chemistry, e.g. cyanogen bromide activation of hydroxy (e.g. cellulosic) carriers or modified carriers, or glutaraldehyde or other dialdehyde coupling to aminogroup containing carriers or modified carriers.

In use, the devices of the invention can be contacted with sample liquid and/or into washing or reagent liquids, for example by dipping. Most conveniently, the devices can contain in impregnated and/or immobilized form, and possibly in distinct zones all of the reagents required by the test in view, so that no contact with separate reagent liquid is needed.

Further illustration of the invention is given by means of the following drawings, and by the undermentioned details of preparation of materials which can be used in fabricating devices according to the invention. The details given below are not intended to limit the invention.

PREPARATIONS OF MATERIALS

A: Selection of liquid-conductive materials:

Representative useful examples of liquid-conductive porous or fibrous sheet materials are as follows, with indications in most cases of pore size, and indications of their relative speed of liquid conduction given as the approximate time taken for aqueous solvent to travel 45 mm in a typical test arrangement:

| Rapidly-conductive materials: | | |
|---|---|---|
| Whatman 3MM | | (about 3 minutes) |
| Whatman 3ET | | (about 1 m 20 sec) |
| Whatman 113 | (30 micron) | (about 0 m 30 sec) |
| Whatman NO4 | (20 micron) | (about 1 m 30 sec) |
| Slower-conductive materials: | | |
| Whatman NO1 | (10 micron) | (about 5 m 40 sec) |
| Whatman NO2 | (7 micron) | (about 5 m 30 sec) |
| Whatman NO50 | (2 micron) | (about 8 m 40 sec) |
| Whatman nitrocellulose | (1 micron) | (about 23 minutes) |
| Whatman nitrocellulose | (5 micron) | (about 19 minutes) |

It is also useful to note that where a particular fibrous sheet has fibres orientated in a predominant axial direction, liquid flow along that axial direction is faster than flow in the transverse direction.

It is mentioned that any of the materials noted as "rapidly-conductive" can be used as the slower conductive track if a more rapidly-conductive material is used as the faster track—and the contrary for the materials noted as slow-conductive. Relative speed is more important, though in general of course it is desirable to have a test device working as fast as can be arranged.

B: Zonal activation and impregnation of liquid-conductive materials:

The materials specified above can be activated for the attachment/immobilization of specific reagents, especially proteins, to limited zones thereof, by any of many methods well-known per se.

For example, paper filter material, e.g. Whatman 31 ET, can be conveniently activated by immersion in 0.2M carbonyldiimidazole in pyridine, with gentle stirring, for 1 hour at room temperature, followed by washing with tetrahydrofuran and blown-air drying, for about 20 seconds.

Alternatively, other sheets with rapid chromatographic properties can be used and activated by methods given in the literature, e.g. those mentioned above, or especially Whatman 3MM, Whatman GFF glass fibre filter paper or suitable synthetic membranes, such as Biodyne A (5 micron pore size) (Trade Marks: available from Whatman and from Pall Corporation respectively).

Liquid-conducting track material with a restricted zone of immobilized protein, especially antibody, can be made for example as follows: A rectangle of Whatman 31 ET paper measuring about 10 cm in length and 10–100 cm in width is activated as described above, and a reaction zone is formed upon it by applying a stripe of material about 0.5–1 cm wide to the activated paper, the stripe being located about half-way along its 10 cm length and extending throughout its 10-100 cm width. The material can for example be a suitably selected antibody preparation, e.g. 100 microgram/ml in pH 9.5 bicarbonate buffer, e.g. selected anti-beta-(human chorionic gonadotrophin) of affinity $K_A$ at least $10^9$, and preferably at least $10^{11}$, suitable for immunoassay of human chorionic gonadotrophin using a second (labelled) anti-HCG antibody in a sandwich format. A small volume of such a preparation can be applied using a fine-tipped pipette, fountain pen, air-brush or TLC applicator to give a stripe of applied liquid yielding a reacted layer approximately 0.5–1 cm wide, which will provide a small immunosorbent area in the completed device. When the applied material has reacted with the activated paper for 1 hour at room temperature, excess activated groups are neutralized in ethanolamine for 1 hour and then washed in 0.1M phosphate buffer pH 7 (0.15M in NaCl) for 1 hour and air-dried at 30° C. Alternatively, the excess activated groups on the paper can be blocked with an inert protein such as BSA or other otherwise inert compound with which the activated groups can react, e.g. polyvinyl alcohol.

Alternatively, Whatman 31 ET material can be activated by contact for 5 hours at room temperature with 0.1M sodium periodate after extensive water-washing. To the activated washed paper, protein is then applied (using the technique described above) in 0.55M borate buffer (pH 8.5, 0.2M in NaCl) and allowed to stand 2 hours at room temperature before contact with a 1 mg/ml solution of sodium borohydride and thorough washing with borate buffer.

The material can then be cut up into numerous strips corresponding to the 10 cm length of the original material, each strip carrying a limited zone of the immobilized antibody to function as an immunosorbent, partway (e.g. about half-way) along its length. In use, this limited zone then becomes a test reaction zone in which the immunoassay reactions take place.

If desired, before cutting up the paper liquid-conductive material into strips, a further reagent stripe can be applied, in the form of a stripe of enzyme-labelled antibody, e.g. alkaline-phosphatase-conjugated anti-HCG, prepared by mixing 100 parts by volume antibody at 3.3 mg/ml concentration to 100 parts by volume alkaline phosphatase at 10 mg/ml concentration. 5 parts by volume 25% polymeric glutaraldehyde are added to the mixture, and the conjugation reaction allowed to continue for 3 hours at (15°–25° C.) ambient temperature. The reaction is stopped by adding 5000 parts by volume buffer (0.05M Tris-HCl, pH 8, with 50 mg/ml ovalbumin, 0.2 mg/ml magnesium chloride, 0.2% sodium azide and 0.2% merthiolate). Before application to the paper, the stock liquid so obtained is diluted 1/20 in 0.1M phosphate-buffered saline (pH 7) containing 0.1% Triton QS9 (Trade Mark—obtainable from Rohm and Haas) detergent.

Liquid-conductive strips can be prepared with an impregnation of other reagents for example enzyme substrate, which in the case of a phosphatase enzyme can conveniently be BCIP substrate at 2 mg/ml in 1M Tris-HCl at pH 9.8, soaked into Whatman No. 1 or Biodyne A (0.5 micron pore size) and air-dried at 30° C.

C: Preparation of liquid-swellable liquid-conductive materials:

Material is used which swells very substantially on addition of water and can be selected from a number of commercially-available alternatives, especially IEF (isoelectric focussing) Wick LKB 1850-911 (from LKB Produkter, Sweden), or lyogel. The isoelectric focussing wick material can expand in height from 1 mm to 2 mm thick on contact with water, i.e roughly double in size. With some materials, especially IEF wick material, it is possible to soak these in substrate solution and dry before assembly of the device.

DETAILED DESCRIPTION OF THE PRESENTLY PREFERRED EXEMPLARY EMBODIMENTS

Figure 1:
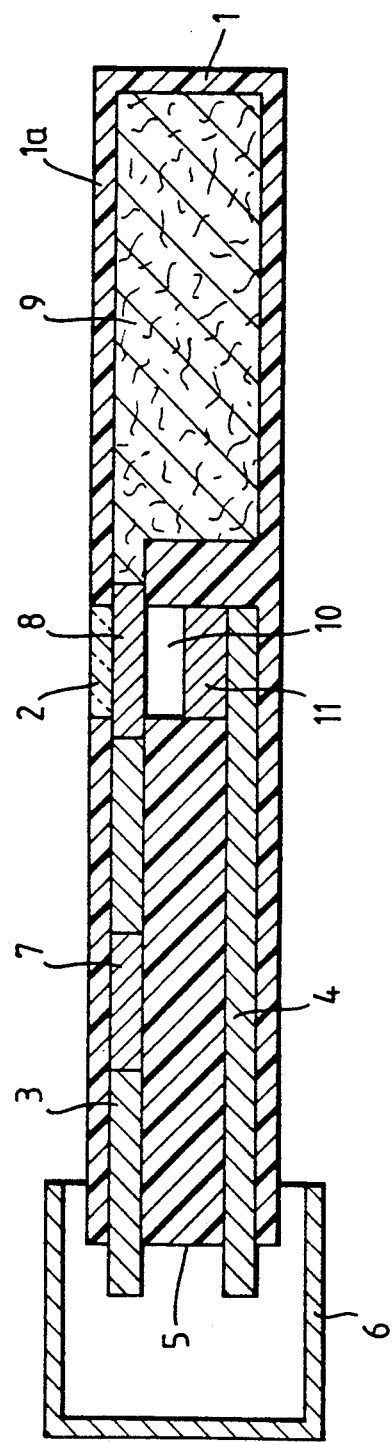
FIG. 1 shows in diagrammatic cross-section a test device according to an embodiment of the invention.

The materials prepared as described above can be used in the fabrication of devices as shown schematically in the drawings.

Referring to FIG. 1, a test device is shown, suitable for carrying out, for example, an enzyme-linked immunoassay and making a colour-change result visible to the user.

The test device comprises a plastics case 1, preferably opaque or translucent, which also acts as a handling-piece at its end 1a. Case 1 has a transparent viewing position 2, through which the user may see an immunosorbent material as described below.

Passing through casing 1 are two passageways or channels 3 and 4 containing conductive tracks of porous or fibrous liquid-conductive material as described above. The channels or passageways and their respective "fast" and "slow" tracks 3 and 4 are open to contact with the outside world at end 5 of casing 1 opposite handle end 1a. In use, end 5 of casing 1, sensitized by the presence of the ends of liquid conductive tracks 3 and 4, is contacted with sample liquid so that both of tracks 3 and 4 take up the sample liquid.

Any convenient arrangement may be included for contacting sensitized end 5 with sample liquid; for example, a urine collection arrangement 6 as described in EP 0 164 180 may be removably fitted to end 5 of casing 1. Another form of sample collection device is a porous body of absorbant material, e.g. of polymeric material, which can rapidly take up an applied liquid sample and then release it into the two tracks; if desired, the porous sample collector can be provided with a removable moisture-impervious cover.

In the device of FIG. 1, track 3 is a relatively fast-conductive track, while track 4 is a relatively slow-conductive track. Track 3 is releasably impregnated at a zone 7 thereof with a conjugate of an enzyme, e.g. alkaline phosphatase, with an antibody, e.g. anti-(human chorionic gonadotrophin), having specificity selected according to the object of the particular test in hand.

A further zone 8 of track 3, farther away from end 5 than zone 7 is, carries covalently-immbolized antibody to confer immunosorbent properties on zone 8 of track 3. Beyond zone 8, track 3 is in liquid-conductive contact with a sink 9 of liquid-absorbent material, e.g. cotton-wool, so that sink 9 can take up liquid that arrives by capillary flow after travelling from its point of uptake at end 5. Sink 9 is accommodated in a cavity in end 1a of casing 1.

Below zone 8 of track 3, a passageway 10 provides communication with track 4, which does not otherwise contact track 3 or sink 9. Before use, there is an air gap, e.g. of the order of up to 1 mm wide, between zone 8 and a "switch" 11 of water-swellable material which is in conductive contact with track 4, and carries (e.g. in an upper layer thereof) a releasable load of impregnated substrate corresponding to the enzyme in zone 7. In use, switch 11 swells by liquid uptake and thereafter makes contact with zone 8.

Use and operation of the device is as follows. The user contacts end 5 with sample liquid. Sample liquid begins to travel along both of tracks 3 and 4, but faster along track 3. Conjugate impregnated at zone 7 is entrained in the liquid flow along track 3. When sample and conjugate reach zone 8 by travel along track 3, immunological binding reactions occur involving the immunosorbent in zone 8, resulting in a variable amount of conjugate becoming bound in zone 8, according to the quantity or concentration of analyte present in the sample liquid, either by "sandwich" complex formation or by competitive binding reaction. Unbound conjugate is washed onwards into sink 9 by continuing flow of sample liquid along track 3. A little later, preferably adjusted by suitable selection of materials and e.g. about 2 minutes later, sample liquid reaches switch 11 after travelling along track 4. This causes switch 11 to swell and make liquid contact with the hinder surface of zone 8 opposite window 2. After this has happened, substrate (e.g. BCIP alkaline phosphatase substrate) from switch 11 flows into zone 8 entrained in liquid supplied by flow along track 4. In zone 8, substrate reacts with bound enzyme according to the quantity of enzyme conjugate immobilized in the binding reaction of the test, and makes a colour change result which is visible through window 2. Continued flow of liquid through tracks 3 and 4 can in certain examples of the device bring about a deceleration or stop to the enzyme reaction in zone 8. Especially advantageously this can be brought about by an advancing front of more acid liquid (e.g. with pH below 7, e.g. in the range 6 or 7) produced by impregnation of part of one of the tracks, e.g. track 4, with suitable buffer, which is entrained in liquid and carried by capillarity to arrive at zone 8 later than the substrate.

Figure 2A:
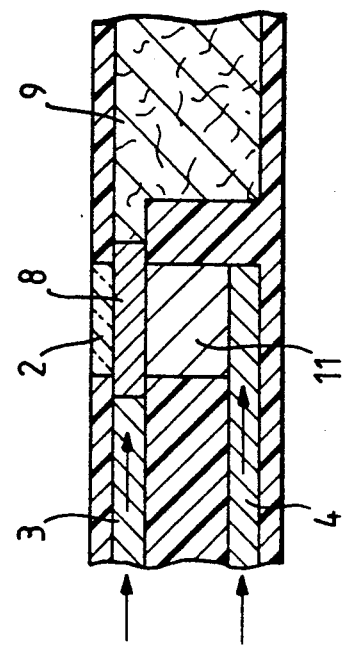
FIGS. 2a and 2b show in diagrammatic section part of the test device according to FIG. 1, before, during and after use respectively.
Figure 2B:
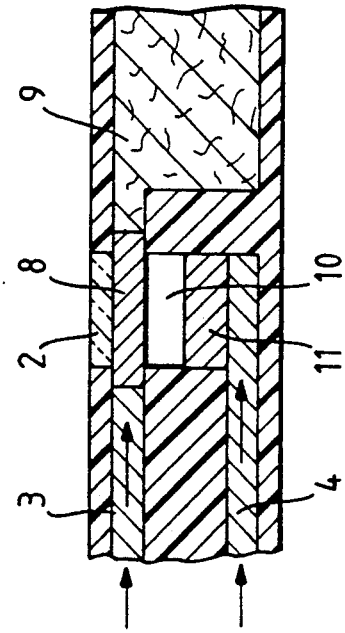

FIGS. 2a and 2b show more clearly the change in configuration of switch 11 during use, as described above.

One of the advantages of this and other embodiments of the invention is that arrangements as described herein can make it unnecessary for the unskilled user, far from sophisticated laboratory facilities, to use analytical washing liquid facilities or even separate liquid water washes: the necessary changes in the liquid environment of the reactive immunosorbent zone can be brought about by the through-flow of sample liquids, e.g. biological or clinical sample liquids including body fluids such as urine.

In a variant part of the device of FIGS. 1-2, counterpart of switch 11 may be omitted, and passageway 10 may from first to last be filled by liquid-conductive material to allow liquid transfer from slow track 4 to zone 8.

The device of FIG. 1 can, for example, be arranged for sandwich immunoassay for an antigen using bound antibody and an enzyme-labelled second antibody. A sampler can be provided to take a liquid sample, mix it with antigen conjugated to detectable label, and apply it as a spot to the upper track. Water can be presented to the free ends of the two tracks, and moves by capillary action through the two tracks. The sample and excess conjugate is washed through the zone of immobilized antibody. In this example the substrate can be presented in the "slow" track and/or in the movable pad of swellable material, in dry form before the device is used, so that it dissolves in the liquids used in the test.

In an alternative arrangement, the conjugate is impregnated on a zone of the fast track and sample is infiltrated in from the left into both tracks, where it functions both as a sample and as wash liquid.

In a further alternative arrangement, the slower track is impregnated with a further reagent so that the wash liquid that infiltrates the carried reagent zone via the slower route, and the swellable filter pad is modified in its composition, e.g. so that it is buffered to a desired acid or alkaline pH that will affect the test reaction, and thereby starts or stops (usually stops) a detection reaction previously taking place in the carried reagent zone.

Figure 3:
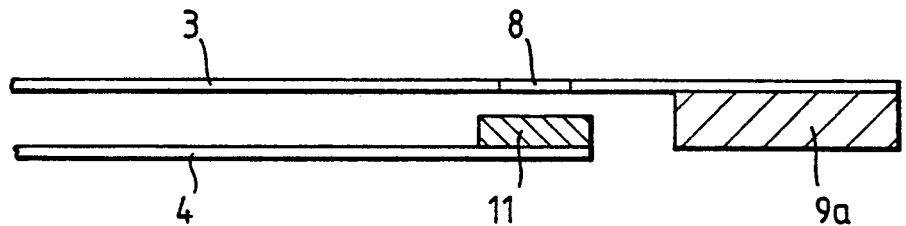
FIGS. 3 to 5 show in diagrammatic fragmentary section, stages in the operation of an alternative embodiment of the test device.
Figure 4:
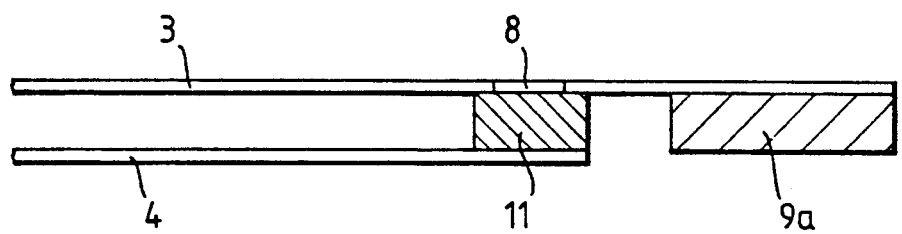
Figure 5:
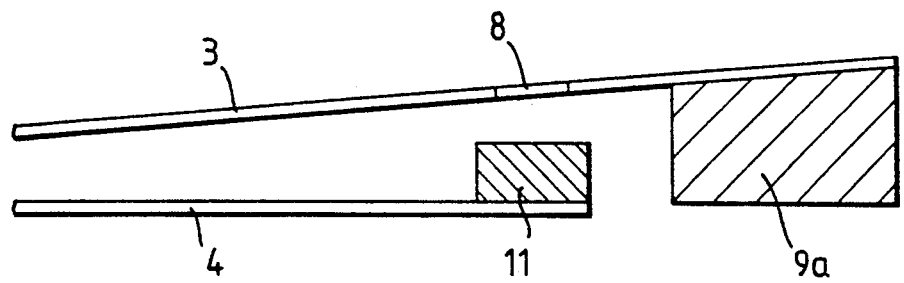

FIGS. 3, 4 and 5 schematically show a development of the features of FIG. 1, in which a further and larger swellable filter pad sink is provided, (in the position of sink 9 in FIG. 1), distant to the point of contact established between the tracks by the first swellable pad described in connection with FIG. 1, and arranged to force the tracks apart when it swells, so re-establishing the air gap and preventing further liquid transfer from the lower to the upper track. FIG. 3 shows the device diagrammatically in its dry state; FIG. 4 after an intermediate stage in use when the first swellable pad has become wetted and swollen by reagent, sample or washing liquid and established contact between the lower and upper tracks; and FIG. 5 after a final stage in which the second swellable pad has swollen and forced the lower and upper tracks apart again, thereby hindering further liquid flow between them.

The invention described herein extends to modifications and variations, as will be apparent to the reader skilled in the art, and extends to all combinations and subcombinations of the features of this description including those of the examples and the accompanying drawings.

We claim:

1. A test device for performing an assay to detect the presence of an analyte in a liquid sample comprising:

a housing;

means within said housing defining first and second separate flow paths for conveying separate liquid streams from a first end of said housing to a reaction zone within said housing, said reaction zone being in fluid contact with said first flow path and carrying in immobilized form, a reagent that specifically binds to said analyte;

liquid absorbent means downstream from and in fluid contact with said reaction zone;

means defining a passage interconnecting said liquid flow paths;

a liquid swellable material disposed within said passage and in fluid contact with said second flow path, said liquid swellable material being adapted to swell on contact with liquid sample thereby to make contact between said liquid flow paths, whereby liquid in said second flow path reaches said reaction zone after liquid in said first flow path reaches said reaction zone; and reagents for detection of bound analyte in the reaction zone incorporated in distinct zones in said first and/or second flow paths or said first and second flow paths are capable of directing said detection reagents to said reaction zone when applied separately to said flow paths.

2. A test device as in claim 1, wherein contact between said first and second liquid flow paths initiates transfer of liquid between said two flow paths, said transferred liquid being selected from the group consisting of a washing liquid and a reagent liquid.

3. A test device as in claim 1, wherein said housing includes a transparent portion through which bound analyte can be visualized in said reaction zone.

4. A test device as in claim 1, wherein said liquid swellable material delivers to said reaction zone an auxiliary reagent which is necessary for visual detection of bound analyte in the reaction zone.

5. A test device as in claim 1, wherein said second flow path delivers to said reaction zone an enzyme substrate for visualization of bound analyte in the reaction zone when an enzyme-linked immunoassay is performed in said test device.

* * * * *